US00PP16893P2

(12) United States Plant Patent
Kawashima

(10) Patent No.: US PP16,893 P2
(45) Date of Patent: Jul. 25, 2006

(54) ***OSTEOSPERMUM* PLANT NAMED 'KAKEGAWA AU15'**

(50) Latin Name: ***Osteospermum* hybrid**
Varietal Denomination: Kakegawa AU15

(75) Inventor: Moriya Kawashima, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/054,764

(22) Filed: Feb. 10, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Jondle & Associates P.C.

(57) ABSTRACT

'Kakegawa AU15' is a new *Osteospermum* cultivar particularly distinguished by its pinkish-purple inflorescence color and compact growth habit.

1 Drawing Sheet

Genus and species: *Osteospermum* hybrid.
Variety denomination: 'Kakegawa AU15'.

BACKGROUND OF THE NEW PLANT

The variety 'Kakegawa AU15' originated from a gene pool population made in Misato, Japan. In May 1999, three *Osteospermum* varieties were intercrossed and $F_1$ seed from this cross was bulked to make the population. The three varieties used in the intercross were 'Purple Passion' (unpatented), an unnamed *Osteospermum* breeding line of unknown origin with white inflorescences and day-neutral blooming, and an unnamed *Osteospermum* line with pink inflorescences.

In April 2000, $F_1$ seed was sown in the greenhouse. Plants were later transplanted outdoors for evaluation in Misato, Japan. Criteria for selection included compact growth habit, day-length neutral flowering, pink inflorescence color and strong vigor. In August 2000, one single-plant selection was made based on the above criteria and vegetatively propagated by rooted cuttings in Misato, Japan. The selection subsequently was named 'Kakegawa AU15' and found to reproduce true to type in successive generations of asexual propagation.

DESCRIPTION OF PHOTOGRAPHS

This new *Osteospermum* plant is illustrated by the accompanying photographs which show blooms and foliage of the plant in full color. The colors shown are as true as can be reasonably obtained by conventional photographic procedures.

DESCRIPTION OF THE NEW CULTIVAR

Figure 1:
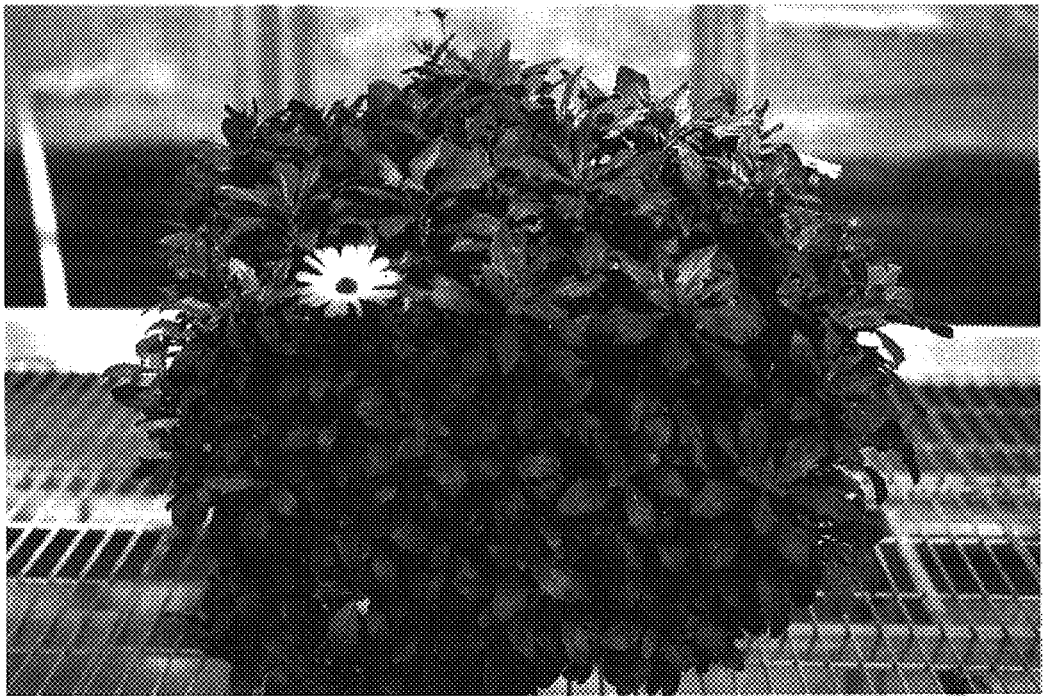
FIG. 1 shows overall plant habit.
Figure 2:
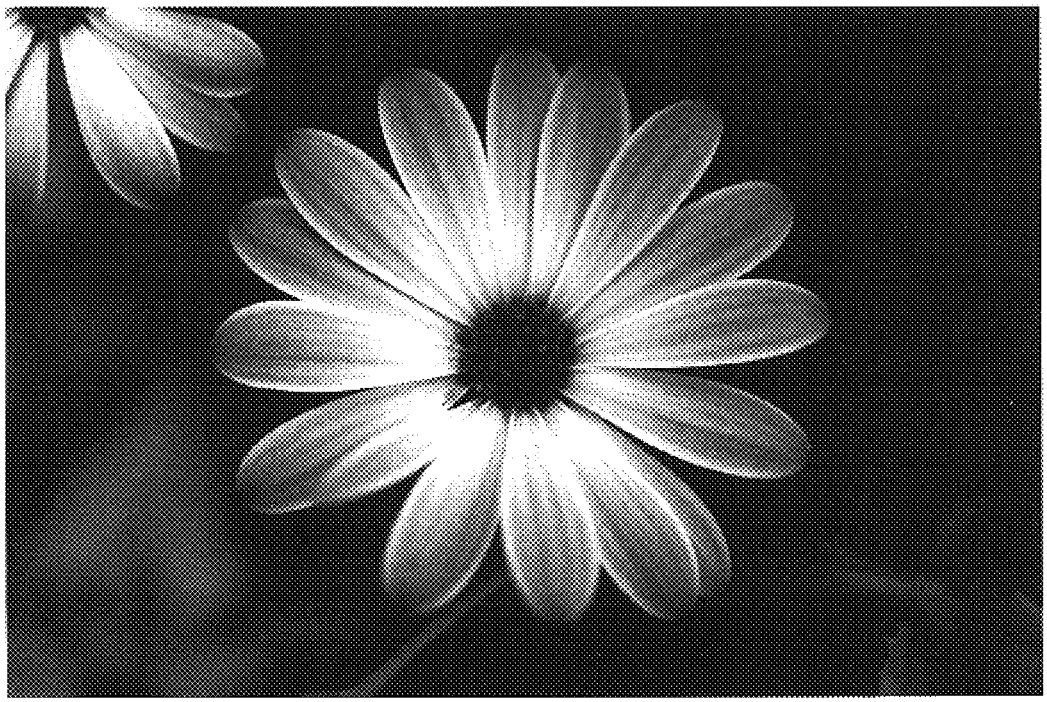
FIG. 2 shows the mature inflorescence.

The following detailed descriptions set forth the distinctive characteristics of 'Kakegawa AU15'. The data which defines these characteristics were collected from asexual reproductions carried out in Salinas, Calif. Data were collected on plants grown about four months from transplanting rooted cuttings into 16 cm diameter pots, one plant per pot, under greenhouse conditions. Color references are to The R.H.S. Colour Chart of The Royal Horticultural Society of London (R.H.S.).

DETAILED BOTANICAL DESCRIPTION

Classification:
- *Family*.—Compositae.
- *Species*.—*Osteospermum* sp. cultivar 'Kakegawa AU15'.

Parentage:
- *Male*.—Unknown *Osteospermum* breeding line.
- *Female*.—Unknown *Osteospermum* breeding line.

*Plant description:*
- *Form*.—Highly branching.
- *Habit*.—Mounding.
- *Height*.—45 cm as measured from soil level to top of plant.
- *Width*.—65 cm.
- *Life cycle*.—Perennial.

Propagation:
- *Type cuttings*.—Vegetative cuttings.
- *Time to produce a rooted cutting*.—About 4 weeks.
- *Time to bloom from propagation*.—About four weeks after transferring a rooted vegetative cutting to a 16 cm diameter pot. Flowering season is all year in the United States. Vernalization is not required to induce flowering.

Environmental conditions for plant growth: The base of each cutting was dipped for one to two seconds in a 1:9 solution of DIP 'N GROW root-inducing solution immediately prior to placing the cutting into a cell tray. The cell tray contained a moistened peat moss-based growing medium. The cuttings were misted with water from overhead hourly until sufficient roots were formed. Rooted cuttings were transplanted and grown individually in 16 cm diameter plastic pots in a glass greenhouse located in Salinas, Calif. Pots contained a peat moss-based growing medium. Soluble fertilizer containing 18% nitrogen, 8% phosphorus and 18% potassium was applied. The soil was allowed to dry between waterings. During the first few weeks after transplanting, the plants were grown under evening temperatures around 15–18° C. for good root growth. When plants reached 7.5–10 cm in height they were pinched back to 5–6 leaves to promote branching. Spring and summer daytime high temperatures in Salinas, Calif. range from 16–25° C.

Stems:

*Texture*.—Slightly pubescent.
*Pubescence color*.—RHS 155A (white).
*Pubescence shape*.—Linear.
*Stem description*.—Ancipital (round) in cross-section.
*Stem color*.—RHS 143C (green).
*Stem diameter*.—1.2 cm at base.
*Internode length*.—1.2–2.0 cm.

Leaves:

*Leaf arrangement*.—Alternate.
*Leaf shape*.—Oblanceolate.
*Leaf apex*.—Mucronate.
*Leaf base*.—Decurrent.
*Leaf margin*.—Serrate.
*Leaf venation*.—Pinnate.
*Leaf texture, both surfaces*.—Dull, smooth.
*Leaf surface pubescence*.—Slight.
*Leaf length*.—5.0–5.6 cm.
*Leaf width*.—1.2–2.7 cm.
*Leaf thickness*.—0.1 cm.
*Leaf color'*.—*Upper surface: RHS* 137'A (green). Lower surface: RHS 137C (green).
*Venation color*.—Upper surface: RHS 144D (yellow-green). Lower surface: RHS 144D (yellow-green).
*Petiole*.—Length: 4.0–5.6 cm. Diameter: 0.2 cm. Color: RHS 144B (yellow-green).

Inflorescence:

*Inflorescence type*.—Capitulum (head); disc florets are perfect and ray florets are carpellate.
*Inflorescence diameter*.—5.5 cm.
*Inflorescence depth*.—2.0 cm.
*Flowering habit*.—Determinate.
*Lastingness of inflorescences*.—3–4 days on the plant.
*Fragrance*.—None.
*Disc floret diameter*.—1.0 cm.
*Disc floret number*.—40–50.
*Phyllaries*.—About 18 in a single whorl per inflorescence, free, arranged symmetrically.
*Phyllary length*.—1.0 cm.
*Phyllary width*.—0.15 cm.
*Phyllary apex*.—Acute.
*Phyllary margin*.—Entire.
*Phyllary shape*.—Lanceolate.
*Phyllary color*.—Upper surface: RHS 143A (green). Lower surface: RHS 143C (green).
*Peduncle length*.—5.5–6.0 cm.
*Peduncle diameter*.—0.1 cm.
*Peduncle color*.—RHS 141D (green).
*Peduncle texture*.—Dull, slight pubescence.

Ray florets:

*Corolla*.—One ray per ray floret; only the outer row of florets is the ray florets.
*Ray floret length*.—2.0–2.3 cm.
*Ray floret width*.—0.6–0.7 cm.
*Ray floret shape*.—Spatulate, curved on the longitudinal axis.
*Ray floret apex*.—Acute.
*Ray floret margin*.—Entire.
*Ray floret color*.—Upper surface: Apex portion is RHS 72D (red-purple); basal portion fades to RHS 155A (white). Lower surface: Apex portion is RHS 186C (gray-purple) with RHS 88B (purple) and RHS 187 (gray-purple) stripes; basal portion fades to RHS 155A (white).
*Ray floret texture*.—Glabrous.
*Ray floret ovary*.—Superior.
*Ray floret pistil form*.—One style with two stigma branches.
*Ray floret pistil length*.—0.4 cm.
*Ray floret stigma color*.—RHS 77A (purple).
*Ray floret style color*.—RHS 155A (white).

Disc florets:

*Disc floret color*.—Upper surface: RHS N77A (purple) at tip fading to translucent at base. Lower surface: RHS N77A (purple) at tip fading to translucent at base.
*Disc floret shape*.—Ensiform.
*Disc floret apex*.—Acute.
*Disc floret base*.—Cuneate.
*Disc floret surface texture*.—Dull, pubescent.
*Disc floret margin*.—Entire.
*Disc floret size*.—Length:0.3 cm. Width: 0.1 cm.
*Disc floret ovary*.—Superior.
*Disc floret pistil form*.—One style with two stigma branches.
*Disc floret style color*.—RHS 155A (white).
*Disc floret stigma color*.—RHS 103A (blue).
*Location of gynoecium*.—Ray florets and disc florets.
*Disc floret stamens*.—5, fused into a single tube.
*Disc floret anther color*.—RHS 103A (blue).
*Disc floret pollen color*.—RHS 25A (orange).
*Location of androecium*.—Disc florets.

DISEASE AND INSECT RESISTANCE

'Kakegawa AU15' is very disease resistant but is susceptible to aphids, thrips, whiteflies and worms.

COMPARISON WITH KNOWN CULTIVARS

'Kakegawa AU15' is a distinct variety of *Osteospermum* owing to its pinkish-purple inflorescence color and compact growth habit. 'Kakegawa AU15' is most similar to the variety 'Seaside' (U.S. Plant Pat. No. 10,782) however, there are differences as described in Table 1 below.

TABLE 1

| Characteristic | 'Kakegawa AU15' | 'Seaside' |
|---|---|---|
| Ray floret color upper surface | Apex portion is RHS 72D (red-purple); basal portion fades to RHS 155A (white) | Apex portion is RHS 73B (purple); basal portion fades to RHS 155C (white) |
| Habit | Compact | Broad |

I claim:

1. A new and distinct cultivar of *Osteospermum* plant as shown and described herein.

* * * * *